United States Patent [19]

Hotta et al.

[11] Patent Number: 4,581,152
[45] Date of Patent: Apr. 8, 1986

[54] WATER-SOLUBLE COOLANT FOR FORMATION OF DRAWN AND IRONED CANS

[75] Inventors: Hisashi Hotta, Yokohama; Toshiyuki Noda, Zama; Yoshiharu Tobita, Kawasaki; Isao Watabiki, Yokohama; Yasu Ishimoto, Tokyo; Takuro Handa, Kashiwa; Masashi Umemura, Saitama, all of Japan

[73] Assignees: Toyo Seikan Kaisha, Ltd.; Asahi Denka Kogyo Kabushiki Kaisha, both of Tokyo, Japan

[21] Appl. No.: 634,209

[22] Filed: Jul. 25, 1984

[30] Foreign Application Priority Data

Jul. 27, 1983 [JP] Japan ................................ 58-135897

[51] Int. Cl.$^4$ ..................... C09K 5/00; C10M 129/66; C10M 137/04; C10M 173/00
[52] U.S. Cl. ................................... 252/78.5; 252/49.3; 252/49.8; 558/105
[58] Field of Search .................... 252/49.3, 49.8, 78.5; 260/950, 978

[56] References Cited

U.S. PATENT DOCUMENTS

| | | |
|---|---|---|
| 2,485,160 | 10/1949 | Niederhauser et al. ............ 549/527 |
| 2,745,846 | 5/1956 | Dazzi ................................. 524/114 |
| 3,256,191 | 6/1966 | Reed et al. ......................... 252/49.8 |
| 3,281,382 | 10/1966 | Kuester et al. ..................... 260/978 |
| 3,282,837 | 11/1966 | Reed et al. ......................... 252/49.8 |
| 3,453,348 | 7/1969 | Demarcq et al. ................... 252/78.5 |
| 3,496,104 | 2/1970 | Shimada et al. .................... 252/49.3 |
| 3,530,205 | 9/1970 | Patton, Jr. et al. ................. 252/78.5 |
| 3,932,290 | 1/1976 | Koch et al. ......................... 252/78.5 |
| 4,243,537 | 1/1981 | Knepp et al. ....................... 252/49.3 |
| 4,384,965 | 5/1983 | Hellsten et al. .................... 252/49.3 |

Primary Examiner—Paul Lieberman
Assistant Examiner—Robert A. Wax
Attorney, Agent, or Firm—Sherman and Shalloway

[57] ABSTRACT

Disclosed is a water-soluble coolant for formation of drawn and ironed cans, which comprises an aqueous solution containing 0.1 to 20% by weight of a phosphorus-containing compound obtained by esterifying an epoxidation product of at least one higher unsaturated fatty acid or its ester with phosphoric acid.

15 Claims, 6 Drawing Figures

4,581,152

WATER-SOLUBLE COOLANT FOR FORMATION OF DRAWN AND IRONED CANS

DESCRIPTION

BACKGROUND OF THE INVENTION (1) Field of the Invention

The present invention relates to a water-soluble coolant for formation of drawn and ironed cans. More specifically, the present invention relates to a water-soluble coolant to be used for cooling and lubrication in manufacturing cans by drawing and ironing a metal blank, especially a tin-deposited steel plate, which is excellent in the cooling and lubricating actions in the drawing and ironing operation conducted at a high speed, which facilitates withdrawal of a can body formed by drawing and ironing from an ironing punch, namely, stripping of a can body, which can be washed away by water alone at the step of washing away the coolant from a can body withdrawn from the ironing punch, and which facilitates the disposal of waste water from the step of washing away the coolant.

(2) Description of the Prior Art

Drawn and ironed cans are widely used as inner pressure cans such as beer cans and carbonated drink cans because they are advantageous in that there is no seam around a can body, the entire surface can be printed, the appearance characteristics are good, the thickness of the side wall portion is small and the amount used of the metal blank can be reduced.

These drawn and ironed cans are manufactured by subjecting a shallow-drawn cup obtained by the drawing operation to ironing between an ironing punch and an ironing die several times. During this ironing operation, it is indispensable that a coolant should be supplied between the the tool and metal blank so as to obtain cooling and lubricating effects.

Aqueous emulsions comprising a mineral oil, a natural oil or fat or a synthetic oil as a base oil and a surface active agent and other additive have been used as the coolant of this type. However, these known coolants are poor in the cooling effect, are not suitable for high-speed production or improvement of the productivity and are defective in that withdrawal (stripping) of can bodies from punches are difficult when these coolants are used. Since the thickness of the side wall portion of a drawn and ironed can is extremely small, if the stripping load (applied in a direction reverse to the processing direction) is increased, buckling is caused on the top of the side wall portion and the can may not be used as a container. Moreover, since water-insoluble components are forcibly dispersed, the adaptability of the coolants to the washing operation is not easy, and therefore, an alkali degreasing step is indispensable. Moreover, a coolant comprising a lubricant of the synthetic oil type, especially a water-soluble lubricant, is defective in that the lubricant contained in waste water can hardly be separated according to a conventional coagulation sedimentation method or activated sludge method.

SUMMARY OF THE INVENTION

It is therefore a primary object of the present invention to provide a water-soluble coolant for formation of drawn and ironed cans, in which the above-mentioned defects of the conventional coolants are eliminated.

Another object of the present invention is to provide a water-soluble coolant comprising a water-soluble lubricating component, which is used in the form of an aqueous composition for cooling and lubrication in the process for manufacturing cans by drawing and ironing metal blanks, especially tin-deposited steel plates, which shows excellent cooling and lubricating effects at the high-speed drawing and ironing operation, which facilitates withdrawal of a can body formed by drawing and ironing from an ironing punch, that is, stripping of a formed can body, which can be washed away by water alone at the step of washing away the lubricant from the can body withdrawn from the ironing punch and which facilitates the disposal of waste water from the washing step.

Still another object of the present invention is to provide a water-soluble coolant for formation of drawn and ironed cans which exerts an excellent anti-corrosive action during and after the forming operation.

More specifically, in accordance with the present invention, there is provided a water-soluble coolant for formation of drawn and ironed cans, which comprises an aqueous solution containing 0.1 to 20% by weight of a phosphorus-containing obtained by esterifying an epoxidation product of at least one higher unsaturated fatty acid or its ester with phosphoric acid.

DETAILED DESCRIPTION OF THE PREFERRED EMBODIMENTS

Figure 1:
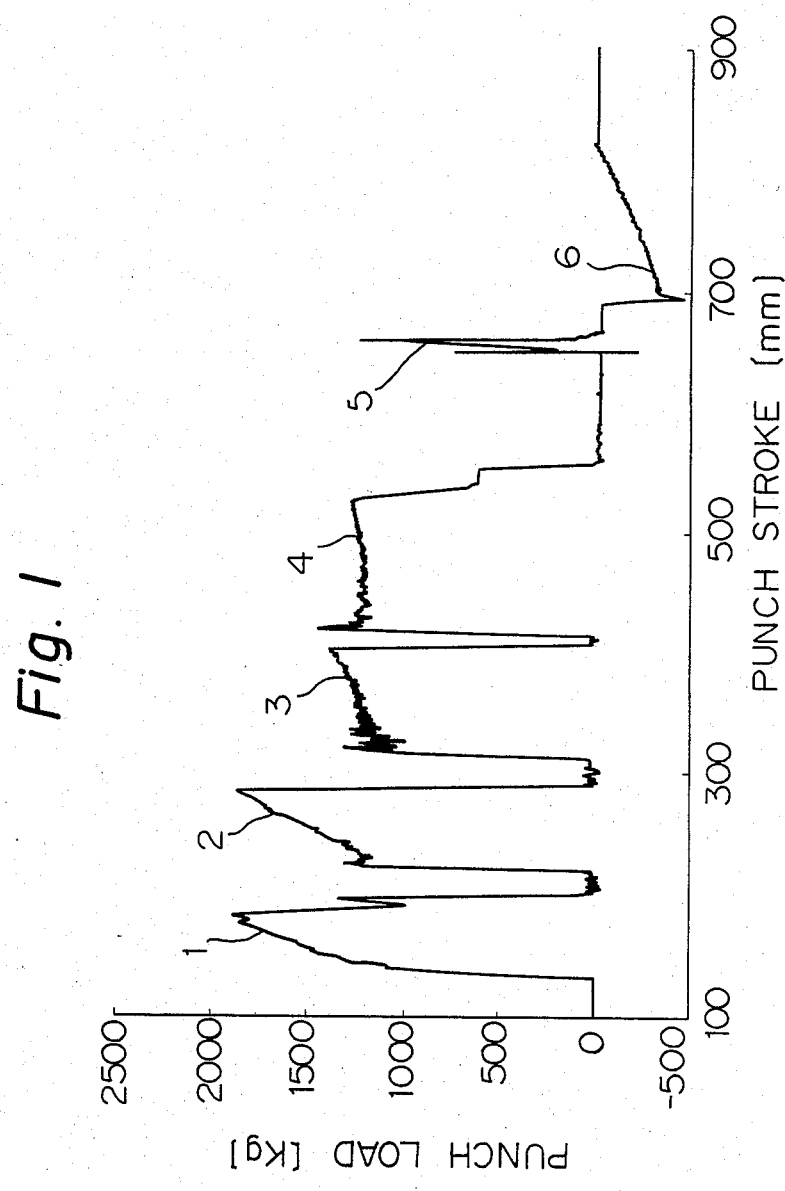
FIG. 1 is a diagram illustrating the relation between a punch stroke distance and a punch load, which is observed when a conventional mineral oil type emulsion is used as a coolant.

The water-soluble coolant of the present invention comprises an aqueous solution containing 0.1 to 20% by weight of a phosphorus-containing compound obtained by esterifying an epoxidation product of at least one higher unsaturated fatty acid or its ester with phosphoric acid.

The phosphorus-containing compound used in the present invention is characterized in that the compound has in one molecule a higher fatty acid portion having oily and lubricating properties and a phosphate portion having water-soluble, high pressure and anti-corrosive properties. In the coolant of the present invention, the lubricating component is present in the state dissolved in water, and therefore, a high cooling effect can be attained. Moreover, since the coolant of the present invention comprises a specific phosphorus compound having the above-mentioned two portions, the boundary lubricating property is excellent, and it is possible to perform the drawing and ironing operation at a high speed. Furthermore, this coolant is advantageous in that increase of the viscosity with elevation of the pressure is controlled to a low level, and the shearing force necessary for breaking the liquid film at the stripping step is small and a good stripping property is attained.

Figure 2:
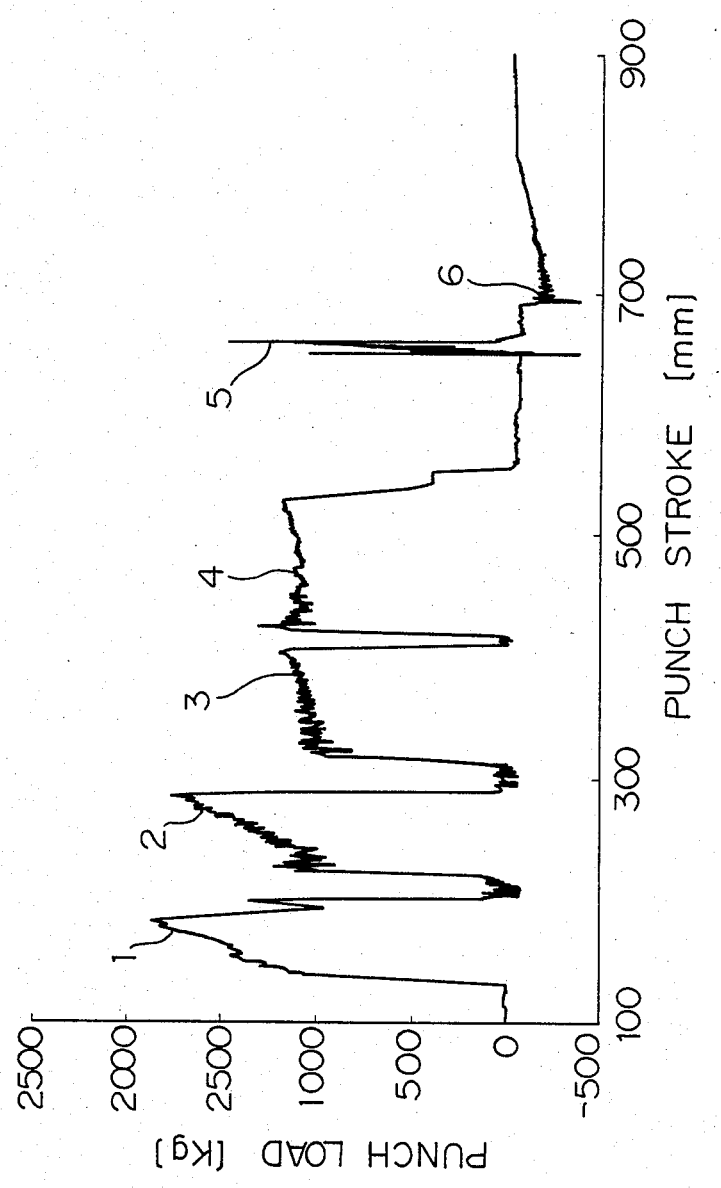
FIGS. 2 and 3 are diagrams illustrating the relation between a punch stroke distance and a punch load, which is observed when the water-soluble coolant of the present invention is used.
Figure 3:
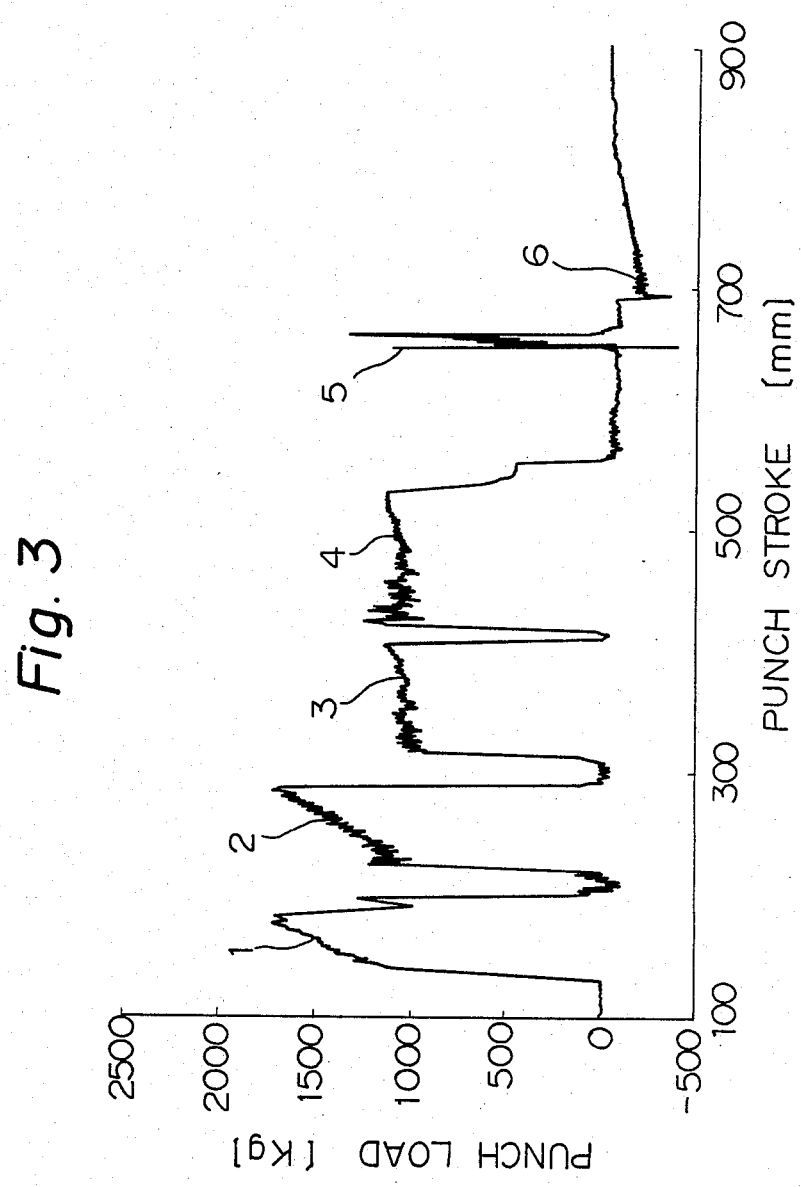

Excellent functional effects of the coolant of the present invention will become apparent from the data illustrated in the accompanying drawings. FIG. 1 is a graph showing the relation between a punch stroke and a punch load observed when a mineral oil type emulsion (sample 1 described hereinafter) is used as the coolant, and FIGS. 2 and 3 are graphs showing similar relations observed when water-soluble coolants according to the present invention are used (samples 2 and 3 described hereinafter). In these graphs, peaks 1, 2, 3 and 4 represent loads applied at the redrawing step, the first ironing step, the second ironing step and the third (final) ironing step, respectively. Furthermore, peak 5 represents a load applied at the step of doming the bottom, and reverse peak 6 represents a load applied at the stripping step. From these data, it will readily be understood that when the water-soluble coolant of the present invention is used, the load applied during the forming operation is controlled to a low level and the load applied at the stripping operation is especially reduced.

A higher unsaturated fatty acid having 14 to 28 carbon atoms is preferred as the higher unsaturated fatty acid used for the phosphorus-containing compound. For example, there can be mentioned mono-unsaturated higher fatty acids such as tzuzuric acid (also known as 4-tetradecenoic acid), physeteric acid, myristolic acid, palmitoleic acid, elaidic acid, petroselinic acid, oleic acid, vaccenic acid, gadoleic acid and erucic acid, and di-unsaturated higher fatty acids such as linoleic acid. Unsaturated higher fatty acids having 16 to 18 carbon atoms are especially preferred.

Monoesters and polyesters of higher unsaturated fatty acids as mentioned above with monohydric alcohols or polyhydric alcohols can be used as the higher unsaturated fatty acid ester. Furthermore, mixtures (for example, oils and fats) comprising a glycerol ester of a higher unsaturated fatty acid as a main component, such as rice bran oil, soybean oil, safflower oil, kapok oil, sunflower oil, rapeseed oil, olive oil, tsubaki oil, cotton seed oil, linseed oil, beef tallow and pig tallow, may be used. Mixtures having an iodine value of 60 to 150 are preferred. For example, rice bran oil, soybean oil, safflower oil, kapok oil, sunflower oil, cotton seed oil and linseed oil are preferred. As another higher unsaturated fatty acid ester, there may be mentioned esters of higher mono-unsaturated acids such as tzuzuric acid, physeteric acid, myristolic acid, palmitoliec acid, elaidic acid, petroselinic acid, oleic acid, vaccenic acid, gadoleic acid or higher di-unsaturated fatty acids such as linoleic acid with monohydric alcohols or polyhydric alcohols. As the monohydric alcohol, there can be mentioned methanol, ethanol, n-propanol, isopropanol, n-butanol, isobutanol, sec-butanol, pentanol, hexanol, heptanol, octanol and 2-ethylhexanol. Monohydric alcohols having 1 to 10 carbon atoms, especially 1 to 3 carbon atoms, are preferred. As the polyhydric alcohol, there can be mentioned ethylene glycol, propylene glycol, diethylene glycol, dipropylene glycol and glycerol.

The process for the preparation of the phosphorus-containing compound used in the present invention will now be described.

At least one compound having an unsaturated group, which is selected from the above-mentioned higher unsaturated fatty acids, higher unsaturated fatty acid esters and unsaturated fatty acid-containing oils and fats, is epoxidized to obtain an epoxidation product. The epoxidation may be carried out according to a customary method using hydrogen peroxide or peracetic acid. The epoxidation ratio is not particularly critical, but it is preferred that the epoxidation ratio be 50 to 90%.

The phosphorus-containing compound used in the present invention can be obtained by phosphatizing the so-obtained epoxidation product with a phosphatizing agent such as ortho-phosphoric acid or polyphosphoric acid. It is preferred that the amount used of the phosphatizing agent be determined so that the obtained phosphorus-containing compound contains 1 to 4 phosphoric acid groups in one molecule (up to two phosphoric acid groups in the fatty acid main chain). A monoester and di-ester of phosphoric acid are formed by phosphatization. The phosphorus-containing compound used in the present invention may contain both the mono-ester and di-ester. The phosphatization is carried out at 10° to 150° C., preferably 20° to 100° C. By-products formed by the phosphatization may be removed by purification using a solvent or the like.

A stable aqueous solution of the obtained phosphorus-containing compound can be obtained by neutralizing the acidic phosphoric acid group with an alkali so that the pH value of the aqueous solution is 6 to 7. As the alkali used as the neutralizing agent, there can be mentioned alkali metal hydroxides such as caustic soda and potassium hydroxide, and alkali metal salts of weak acids such as sodium carbonate, potassium carbonate and lithium carbonate. Furthermore, an amine type neutralizing agent such as methylamine, ethylamine or propylamine may be used.

The phosphorus-containing compound of the present invention is used in the form of an aqueous solution containing the compound in an amount of 0.1 to 20% by weight, preferably 0.5 to 10% by weight, as the pure component. If the content of the phosphorus-containing compound is lower than 0.1% by weight, the lubricating effect is insufficient, and even if the phosphorus-containing compound is incorporated in an amount exceeding 20% by weight, no substantial improvement of the effect can be expected.

The coolant of the present invention may further comprise water-soluble oiling agents, anti-corrosive agents, defoaming agents and antioxidants. Moreover, it is preferred that a mildew-proofing agent be added when the coolant of the present invention is used.

When the water-soluble coolant is applied to a punch, a die or a can body by spraying through a nozzle, dipping or spray coating at the step of draw-ironing a tin-deposited steel plate, the intended lubricating and cooling effects can be attained. This coolant can be used repeatedly, if necessary after cooling or filtration. The formed can body can easily be stripped from the ironing punch and water washing of the can body can easily be accomplished by dipping the can body in warm water or spraying warm water to the can body. The water-soluble coolant of the present invention is advantageous in that the disposal of waste water from the washing step can easily be accomplished. Namely, if this waste water is treated according to a coagulating separation method using an aluminum type or aluminum-iron type coagulant such as aluminum sulfate, ferric sulfate or polyaluminum chloride, slaked lime, and a polymeric coagulant singly or in combination, pollutants can be substantially removed. If necessary, the waste liquid after separation of the sludge may be subjected to an activated sludge treatment, whereby removal of pollutants is made more complete.

The present invention will now be described in detail with reference to the following examples that by no means limit the scope of the invention.

PRODUCTION EXAMPLE 1

A 1-liter 4-neck flask was charged with 231 g (2.0 moles) of 85% ortho-phosphoric acid (first class grade chemical), and 660 g (2.0 moles) of epoxidized ethyl stearate was added dropwise at 55° to 65° C. in a nitrogen current and the mixture was stirred at 55° to 65° C. for 1 hour and then cooled. The reaction product was extracted with ether and washed with water, and the ether was removed to obtain an acidic phosphoric acid ester having an acid value of 165. The acidic phosphoric acid ester was neutralized with a 20% aqueous solution of caustic soda so that the pH value was 6.5, whereby product I was obtained.

The physical properties of the product I are shown in Table 1.

PRODUCTION EXAMPLE 2

A 3-liter 4-neck flask was charged with 570 g (6.4 moles) of 110% polyphosphoric acid and 570 g of ethyl ether to form a solution, and 1860 g (2.0 moles) of epoxidized soybean oil was dropped into the solution in a nitrogen current at 40° to 50° C. The mixture was stirred at 40° to 50° C. for 1 hour and then cooled. The reaction product was washed with water and the ether was removed to obtain an acidic phosphoric acid ester having an acid value of 160. The acidic phosphoric acid ester was neutralized with a 20% aqueous solution of caustic soda so that the pH value was 6.5 to 7.0, whereby product II was obtained.

The physical properties of the product II are shown in Table 1.

TABLE 1

| Physical Properties | Product I | Product II |
| --- | --- | --- |
| pH Value | 6.85 | 6.56 |
| Friction coefficient (pendulum test, 25° C.) | 0.095 | 0.089 |
| Surface tension (dynes/cm) (25° C.) | 34.6 | 32.5 |
| Foaming power (Weeks method) | small | small |
| Anti-corrosive property | good | good |
| BOD (mg/l) | 280000 | 270000 |
| COD (mg/l) | 130000 | 121000 |

Foaming power, Corrosiveness, BOD and COD were determined according to the Japanese Industrial Standards (JIS). BOD and COD refer to Biological Oxygen Demand and Chemical Oxygen Demand, respectively.

EXAMPLE

Water-soluble coolants were prepared by diluting the products I and II with water.

These water-soluble coolants were tested according to methods described below to obtain results shown below.

I. Forming and Stripping Properties

(1) Cup-Forming Property

Draw-forming was carried out under the following conditions by using the above-mentioned water-soluble coolants.
Plate thickness: 0.30 mm
Hardness (Rockwell 30T): 55.0
Amount of tin deposited on surface to be formed into outer face of can: 2.8 g/m$^2$
Amount of tin deposited on surface to be formed into inner face of can: 2.8 g/m$^2$
Inner diameter of drawn can: 71 mm
Height of drawn can: 34 mm
Forming speed: 120 cans/min

(2) Adaptability to Ironing

The drawn cup formed under the conditions described in (1) above was re-drawn in a known ironing apparatus and subjected to first stage ironing (thickness reduction ratio of 38.2%), second stage ironing (thickness reduction ratio of 13.6%) and third stage ironing (thickness reduction ratio of 39.4%) to obtain a can having an inner diameter of 52.66 mm, a height of 145.0 mm, a thickness of 0.100 mm in the main portion of a can body and a thickness of 0.160 mm in an end portion of the opening (having a length of about 20 mm from the end portion of the opening), and the can was withdrawn from the forming punch by a stripper. The forming speed was 200 cans/min.

Withdrawal of the can body from the ironing punch was accomplished according to the following procedures.

A stripper having many annularly arranged claws was attached to the near of the portion to which the final ironing die (the third stage ironing die in this Example) was attached. The end of the opening of the formed can body, which was capped on the forming punch and retreated together with the forming punch being retreated to the position before the ironing operation, was caused to impinge against the stripper, and the retreat of the can body was blocked while only the punch was retreated. (At this operation, compressed air was auxiliarily blown to the bottom of the can body from the top end of the punch.)

A load cell provided with a strain gauge was attached between the forming punch and a ram to which said punch was attached, so that the force loaded on the punch could be measured. The force applied at the ironing step and the force applied to the open end of the can from the stripper at the stripping step were measured by the load cell, and the measured forces were processed to numerical values so that numerical values of the stripping loads could be read.

The cup-forming property, adaptability to ironing and stripping property were evaluated as follows.

(1) Cup-forming property

○: forming possible without breakage
X: forming impossible because of breakage

(2) Adaptability to ironing

⊙ : ironing possible without flaws
○: ironing possible but flaws observed
X: ironing impossbiel because of breakage

(3) Stripping Property (i) Buckling on end edge of opening of can withdrawn by stripper ⊙ : no buckling on end edge of opening of can
○: buckling caused only on ear portion of end edge of opening of can but not extended to trough portion
Δ: buckling caused on end edge of opening, which was not extended to trimming line at next trimming step
X: buckling caused on end edge of opening, which was extended to trimming line at next trimming step (ii) Stripping load The adaptability to the stripping operation was evaluated according to the stripping load imposed on the ironing punch.

2. Washing Property

A cold-drawn steel plate of 6 mm × 8 mm specified by JIS G-3141 was used. The steel plate was dipped in a 10% aqueous solution of the coolant for 5 seconds and dried for 5 hours outdoors. The so-formed sample steel plate was washed with city water at 12 l/min, and after draining, the washing property was evaluated according to the following scale.

⊙ : wetted completely with water
○: higher than 75%
Δ: 50–75%
X: lower than 50%

3. Anti-corrosive Property

A sample steel plate prepared in the same manner as described in the preceding Section 2 was hung outdoors for 24 hours and the rusting state was checked, and the anti-corrosive property was evaluated according to the following scale based on the method of JIS K-2246.
⊙ : no rusting
○ : 10% or less
Δ: 11–25%
X: 26–50%
XX: 51% or more 4. Adaptability to Waste Water Treatment Slaked lime was added to washing waste water from a can washing machine in a mixing tank so that the pH value was substantially at a neutral level, and then, ferric chloride and a polymeric coagulant were added to the waste water to form flocs. The flocs were removed and BOD and COD of the remaining water were measured.

For comparison, a self-emulsifiable lubricant having a composition described below was diluted to a predetermined concentration, and the resulting emulsion type coolant was tested in the same manner as described above.

| Recipe of Conventional Lubricant (Comparison) | |
|---|---|
| Mineral oil | 75% |
| Triethylene glycol caprate caprylate | 14% |
| Polyoxyethylene lauryl ether | 4% |
| Oleic acid | 7% |

The obtained results are shown in Table 2.

TABLE 2

| Sample No. | Lubricant | Concentration (%) | Cup-Forming Property | Adaptability to Ironing | Stripping Property buckling resistance | Stripping Property load (kg) | Washing Property | Anti-Corrosive Property |
|---|---|---|---|---|---|---|---|---|
| 1 | emulsion type | 6 | ○ | ⊙ | ○~Δ | 419 | X | ⊙ |
| 2 | product I | 1 | ○ | ⊙ | ⊙~ | 300 | ⊙ | ⊙ |
| 3 | product II | 1 | ○ | ⊙ | ⊙~ | 291 | ⊙ | ⊙ |
| 4 | emulsion type | 1 | X | ○ | Δ~X | 520 | X | ⊙ |
| 5 | product I | 2 | ○ | ⊙ | ○~ | 290 | ⊙ | ⊙ |
| 6 | product I | 0.5 | ○ | ⊙ | ○~ | 313 | ⊙ | ⊙ |
| 7 | product II | 0.5 | ○ | ⊙ | ○~ | 305 | ⊙ | ⊙ |
| 8 | product II | 5 | ○ | ⊙ | ○~ | 285 | ⊙ | ⊙ |

Figure 4:
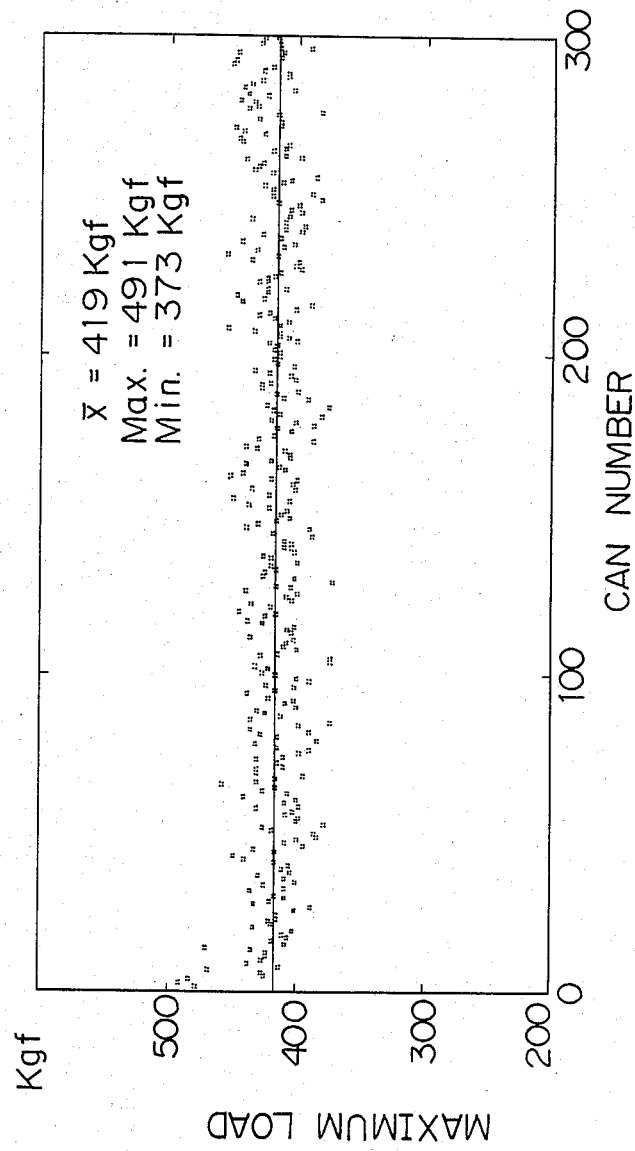
FIG. 4 is a diagram showing the dispersions of the maximum load and can number at the stripping step, which are observed when the emulsion type coolant used for obtaining the results shown in FIG. 1 is used.
Figure 5:
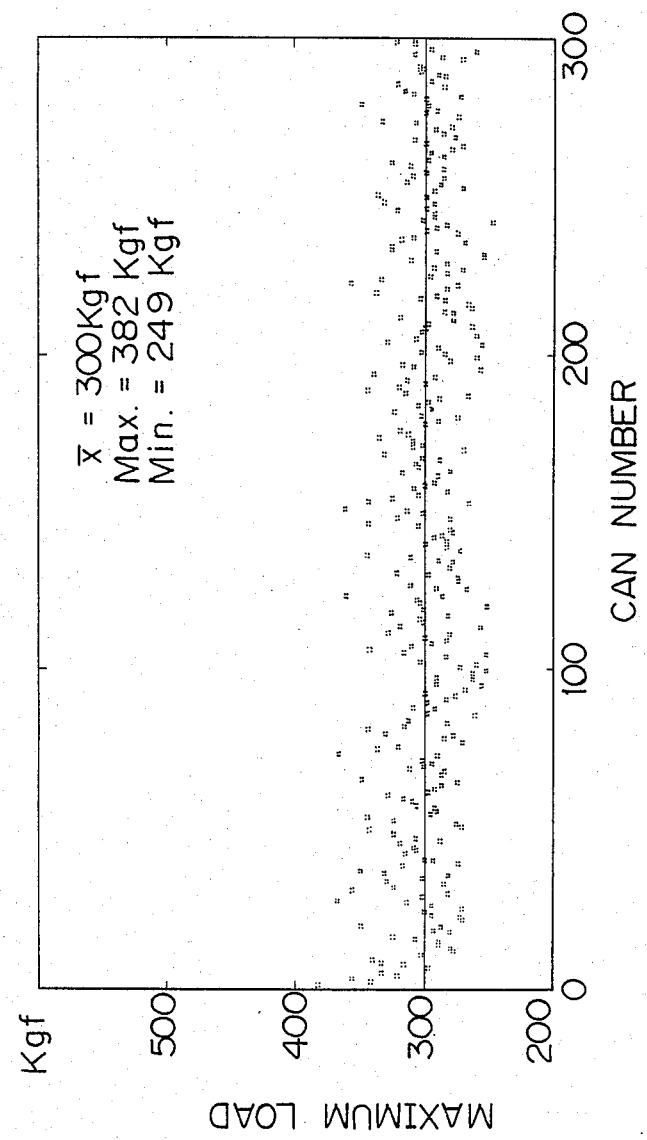
FIGS. 5 and 6 are diagrams illustrating the dispersions of the maximum load and can number at the stripping step, which are observed when the water-soluble coolant of the present invention is used.
Figure 6:
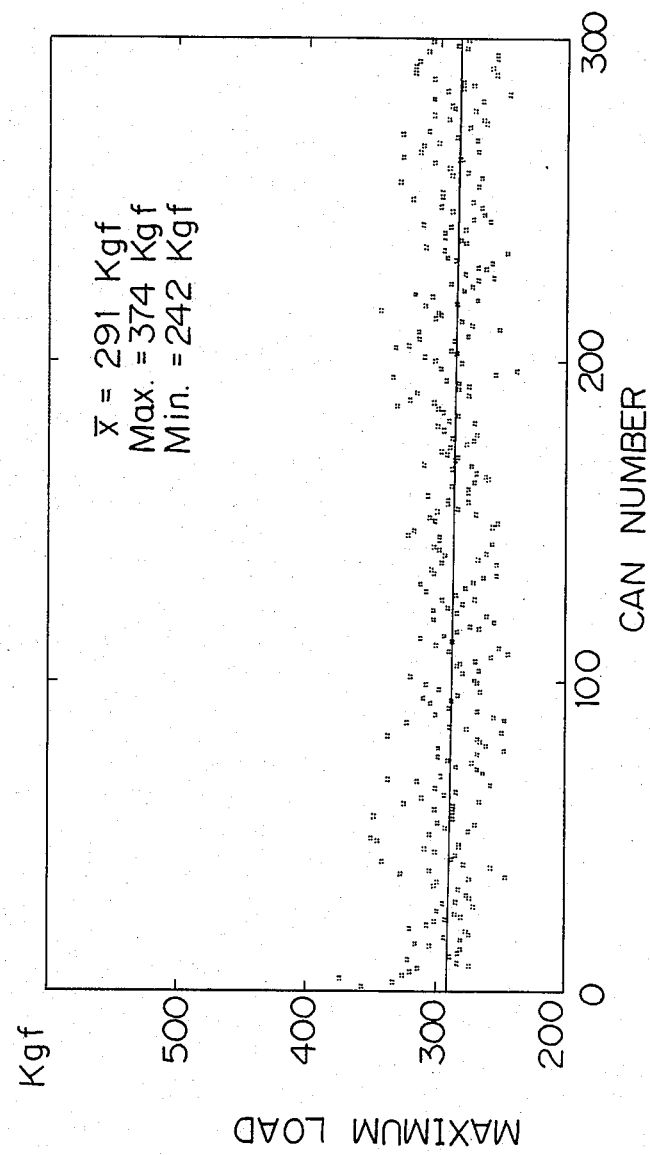

With respect to each of samples 1 through 3, 300 cans were continuously formed, and the stripping force was measured in each can and the maximum force at the stripping step was plotted. The obtained results are shown in FIG. 4 (emulsion type sample 1), FIG. 5 (sample 2 of product I) and FIG. 6 (sample 3 of product II).

The results of the waste water treatment test made on sample 2 are shown in Table 3.

TABLE 3

| Concentration (mg/l) of Coolant | Analysis Item | Quality (mg/l) of Raw Water | Coagulating Separation Quality (mg/l) of Treated Water | Coagulating Separation Removal Ratio (%) | Biological Treatment Quality (mg/l) of Treated Water | Biological Treatment Average Water Quality (mg/l) | Biological Treatment Removal Ratio (%) |
|---|---|---|---|---|---|---|---|
| 500 | BOD | 301.0 | 92.0 | 69.4 | 4.7–25.5 | 16.2 | 82.4 |
| | COD | 251.0 | 51.0 | 79.7 | 31.7–39.5 | 33.8 | 33.7 |
| | SS | — | — | — | 32.3–40.0 | 35.3 | — |

We claim:

1. A water-soluble coolant for formation of drawn and ironed cans, which comprises an aqueous solution containing 0.1 to 20% by weight of a phosphorus-containing compound obtained by esterifying an epoxidation product of at least one higher unsaturated fatty acid having from about 14 to about 28 carbon atoms or its ester with a monohydric or polyhydric alcohol with phosphoric acid.

2. A water-soluble coolant as set forth in claim 1, wherein the higher unsaturated fatty acid is one having 16 to 18 carbon atoms.

3. A water-soluble coolant as set forth in claim 1, wherein the higher unsaturated fatty acid ester is a mixture containing a glycerol ester of said higher unsaturated fatty acid as a main component and having an iodine value of 60 to 150.

4. A water-soluble coolant as set forth in claim 3, wherein the glycerol ester is rice bran oil, soybean oil, safflower oil, kapok oil, sunflower oil, cotton seed oil or linseed oil.

5. A water-soluble coolant as set forth in claim 1, wherein the monohydric alcohol is one having 1 to 10 carbon atoms.

6. A water-soluble coolant as set forth in claim 5, wherein the monohydric alcohol is one having 1 to 3 carbon atoms.

7. A water-soluble coolant as set forth in claim 1, wherein the polyhydric alcohol is ethylene glycol, propylene glycol, diethylene glycol, dipropylene glycol or glycerol.

8. A water-soluble coolant as set forth in claim 1, wherein the phosphorus-containing compound contains 1 to 4 phosphoric acid groups in one molecule.

9. A water-soluble coolant as set forth in claim 1, wherein the pH value of the aqueous solution is adjusted to 6 to 7 by a neutralizing agent.

10. A water-soluble coolant as set forth in claim 9, wherein the neutralizing agent is an alkali metal hydroxide, an alkali metal salt of a weak acid or an amine.

11. A water-soluble coolant as set forth in claim 1, wherein the content of the phosphorus-containing compound in the aqueous solution is 0.5 to 10% by weight.

12. A water-soluble coolant as set forth in claim 1, further comprising a water-soluble oiling agent, an anticorrosive agent, a defoaming agent, an antioxidant, a mildew-proofing agent, or mixtures thereof.

13. The water-soluble coolant of claim 1 wherein the epoxidation product has an epoxidation ratio of from 50 to 90%.

14. A water-soluble coolant useful in the formation of drawn and ironed cans and which is removable as a pollutant from waste water using one or more of an aluminum, aluminum iron, slaked lime or polymeric coagulant, said coolant comprising an aqueous solution containing 0.1 to 20% by weight of a lubricating compound which is a mono-, or di-ester or mixture of mono- and di-esters of the epoxidation product of at least one unsaturated group containing compound selected from the group consisting of tzuzuric acid, physeteric acid, myristolic acid, palmitoleic acid, elaidic acid, petroselinic acid, oleic acid, vaccenic acid, gadoleic acid, erucic acid, linodeic acid, esters of any of said acids with a monohydric or polyhydric alcohol, and unsaturated fatty acid-containing oils and fats, with a phosphatizing agent selected from the group consisting of ortho-phosphoric acid and polyphosphoric acid, said lubricating component containing from one to four phosphoric acid groups.

15. The water-soluble coolant of claim 14 further comprising a neutralizing agent in an amount such that the aqueous solution has a pH in the range of from about 6 to about 7.

* * * * *